United States Patent [19]

Mathies et al.

[11] Patent Number: 5,436,130
[45] Date of Patent: Jul. 25, 1995

[54] MULTIPLE TAG LABELING METHOD FOR DNA SEQUENCING

[75] Inventors: Richard A. Mathies, Contra Costa County; Xiaohua C. Huang, Mt. View; Mark A. Quesada, San Francisco, all of Calif.

[73] Assignee: The Regents of the University of California, Oakland, Calif.

[21] Appl. No.: 143,377

[22] Filed: Oct. 26, 1993

Related U.S. Application Data

[63] Continuation of Ser. No. 854,375, Mar. 19, 1992, abandoned.

[51] Int. Cl.[6] .................. C12Q 1/68; C12P 19/34; G01N 33/50
[52] U.S. Cl. ........................ 435/6; 435/91.5; 436/94; 436/164; 436/172; 436/173; 935/77
[58] Field of Search ............... 435/6, 915; 436/164, 436/172, 173; 935/77

[56] References Cited

U.S. PATENT DOCUMENTS

| | | | |
|---|---|---|---|
| 4,811,218 | 3/1989 | Hunkapiller et al. | 364/413.01 |
| 4,833,332 | 5/1989 | Robertson et al. | 250/458.1 |
| 5,003,059 | 3/1991 | Brennan | 536/27 |
| 5,124,247 | 10/1992 | Ansorge | 435/6 |

FOREIGN PATENT DOCUMENTS 2155176  5/1988  United Kingdom .

OTHER PUBLICATIONS

Prober et al. Science (1987) 238:336–341.
Zagursky, R. BioTechniques (1990) 9:74–79.
Smith, L. et al. Methods in Enzymology (1987) 155:260–301.
Prober, et al., *Science* 238, 336 (1987), A System for Rapid DNA Sequencing with Fluorescent Chain-Terminating Dideoxynucleotides.
Smith, et al., *Nature* 321, (Jun. 1986), Fluoresence detection in automated DNA sequence analysis.
Hernandez, et al., *Journal of Chromatography* 502, 247–255 (1990), Detection and quanntification of capillary electrophoresis zones by fluoresence microscopy.
Zoler, M. L., *Biotechnology* vol. 3, 395–396 (May 1985), CalTech Develops New DNA Sequencing Method.

*Primary Examiner*—Margaret Parr
*Assistant Examiner*—Carla Myers
*Attorney, Agent, or Firm*—Flehr, Hohbach, Test, Albritton & Herbert

[57] ABSTRACT

A DNA sequencing method described which uses single lane or channel electrophoresis. Sequencing fragments are separated in said lane and detected using a laser-excited, confocal fluorescence scanner. Each set of DNA sequencing fragments is separated in the same lane and then distinguished using a binary coding scheme employing only two different fluorescent labels. Also described is a method of using radio-isotope labels.

22 Claims, 4 Drawing Sheets

|   | DYE 1 | DYE 2 |
|---|---|---|
| A | 1 | 1 |
| G | 0 | 1 |
| T | 1 | 0 |
| C | 0 | 0 |

FIG.−2

|   | DYE 1 MOLE FRACTION | DYE 2 MOLE FRACTION |
|---|---|---|
| A | 1 | 0 |
| G | 1/2 | 1/2 |
| T | 1/3 | 2/3 |
| C | 0 | 1 |

FIG.−5

MULTIPLE TAG LABELING METHOD FOR DNA SEQUENCING

This invention was made with U.S. Government support under Grant Contract No. DE FG 91ER61125 awarded by the Department of Energy. The U.S. Government has certain rights in this invention.

This is a continuation of application Ser. No. 07/854,375 filed Mar. 19, 1992, now abandoned.

BRIEF DESCRIPTION OF THE INVENTION

This invention relates generally to a multiple tag labeling method for DNA sequencing and more specifically to a capillary array electrophoresis apparatus that uses a two-channel fluorescence detection system employing multiple dye labeling.

BACKGROUND OF THE INVENTION

Current automated DNA sequencing methods use fluorescence detection of labeled DNA sequencing fragments. One method is to form four sets of DNA sequencing fragments terminating in G, A, T or C where each set is labeled with the same fluorophore, and then run the sequencing fragment sets in adjacent lanes in a slab gel electrophoresis apparatus. Various apparatus have been suggested for scanning the gel to monitor said fragments as or after they move through the gel. In copending application Ser. No. 07/531,900 filed Jun. 1, 1990, U.S. Pat. No. 5,091,652, incorporated herein by reference, there is described a laser-excited confocal fluorescence gel scanner which provides enhanced detection of fluorescently labeled DNA sequencing fragments separated on a slab gel.

The detection system uses an epi-illumination format where the laser power is focused on the sample by a microscope objective followed by confocal detection. However, lane-to-lane variations in the migration velocity of the DNA fragments make it difficult to deduce the correct alignment of the bands in the four sequencing lanes. The throughput is reduced because of the need for running four lanes to detect the four sets of DNA sequencing fragments terminating in G, A, T and C.

A solution proposed to overcome these drawbacks is to label each sequencing fragment set with a different fluorophore, and then to perform the electrophoresis operation in only one lane. This requires a multi-color detection system and dyes that do not alter the mobility of the fragments relative to one another. A method and apparatus for sequentially scanning four colors in multiple lanes in a slab gel is described in U.S. Pat. No. 4,811,218 and by Smith, et al., *Nature* 321,674 (1986). An alternative method using four different dye labeled dideoxy terminators along with two-color detection has been described in U.S. Pat. No. 4,833,332 and by Probet et al. *Science* 238, 336 (1987).

Capillary electrophoresis is emerging as a high-speed DNA sequencing method. In copending application Ser. No. 07/840,501 filed Feb. 24, 1992, U.S. Pat. No. 5,274,240, there is described an automated sequencing apparatus which employs an epi-illumination format where a laser is focused to a small volume by a microscope objective and fluorescence emitted from said volume is gathered by the same objective followed by confocal detection. An array of side-by-side parallel capillaries is sequentially and periodically moved past the focal volume or vice versa to cause and detect fluorescence in labeled DNA sequencing fragments within the capillaries. The capillary array electrophoresis scanner is described in said application for use in a one-color, single-channel detection system where each set of DNA sequencing fragments is separated in a separate capillary or in a four-color, four-channel detection system where each set of fragments is labeled with a different fluorophore for separation and detection in only one capillary.

It is very difficult, in practice, to find four dyes of exactly the same electrophoretic shift. Therefore, it becomes necessary to perform complicated shift corrections before the sequence can be read. Four-color detection has been described in connection with capillary electrophoresis by Smith and coworkers using a simultaneous four-color detection system where the signal is split between each of four channels (Nucleic Acids Research 18, 4417–4421 (1990)). This is satisfactory, but the signal-to-noise ratio is reduced because the signal is split between four different channels, and the problem of maintaining equal band shifts for each of the sets of labeled sequencing fragments using different dyes must still be resolved.

OBJECTS AND SUMMARY OF THE INVENTION

It is an object of this invention to provide an improved DNA sequencing apparatus and method.

It is another object of this invention to provide a DNA sequencing method in which each set of sequencing fragments is labeled with two different fluorescent dyes.

It is yet another object of this invention to provide a DNA sequencing method in which the sets of sequencing fragments are labeled with fluorescent dyes having substantially the same mobility shift.

It is another object of the invention to provide a sequencing method in which the sequencing fragments are labeled with different fluorescent dyes and the ratio of the fluorescent signals in two different detection wavelength regions is employed to detect the fragments.

The foregoing and other objects of the invention are achieved by a multi-color electrophoresis scanning apparatus which employs labeling selected DNA sequencing fragments with different mole fractions of fluorophores, electrophoresing the labeled sequencing fragments in a single lane to cause separation by sizes and determining the position of said fragments in the overall sequence by detecting the ratio of intensity of fluorescence at two detection wavelengths from said labeled fragments.

BRIEF DESCRIPTION OF THE DRAWINGS

The foregoing and other objects of this invention will be more clearly understood from the following description when read in conjunction with the accompanying drawings, in which:

FIG. 2 shows a two-color DNA fragment fluorophore coding method;

FIG. 5 shows another two-color DNA fragment fluorophore coding method.

DETAILED DESCRIPTION OF DRAWINGS

Figure 1:
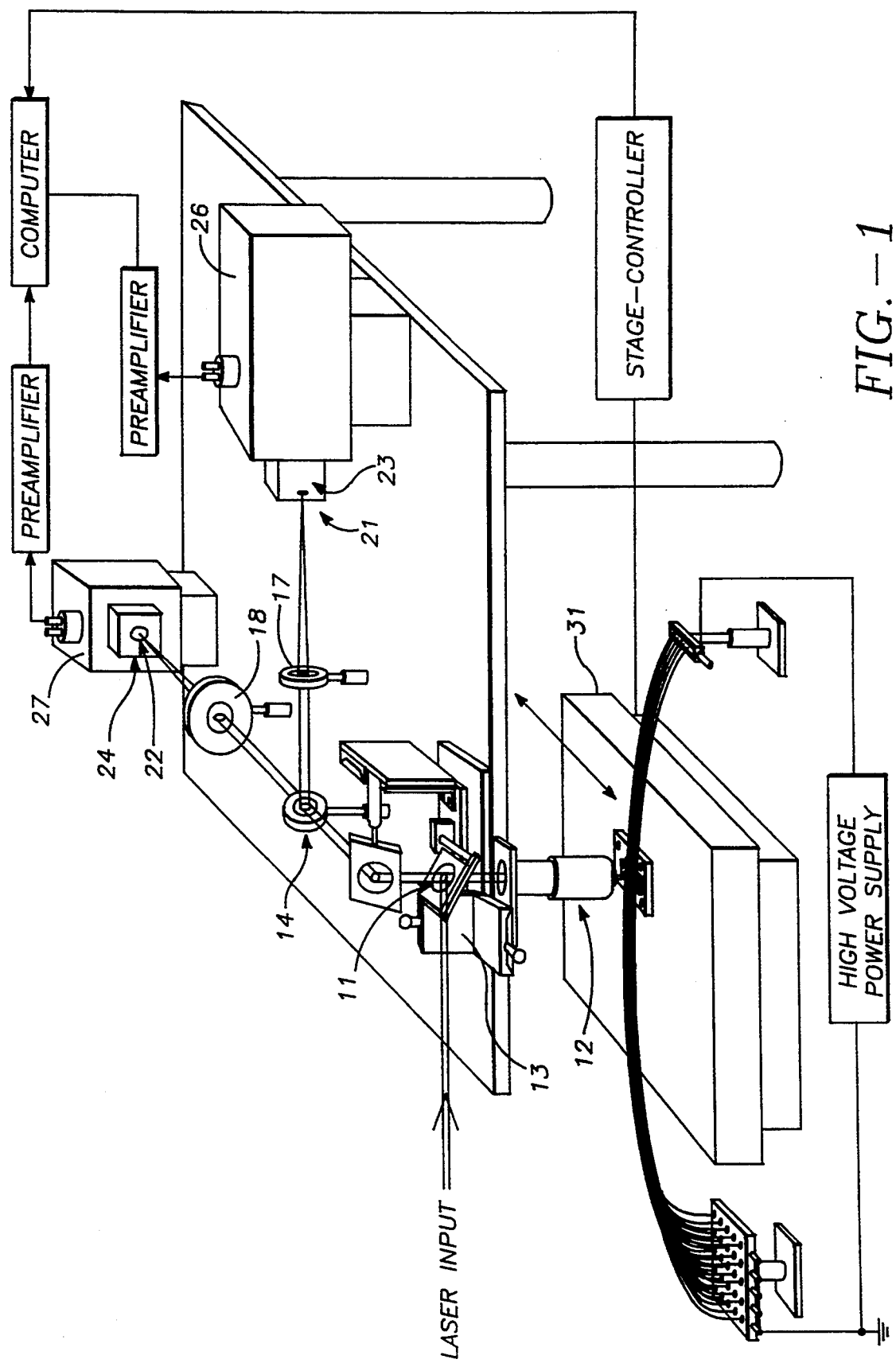
FIG. 1 shows a two-color, capillary array electrophoresis scanner in accordance with the invention.

A suitable, two-color capillary array electrophoresis scanner for detecting DNA sequencing is shown in FIG. 1. It consists of two confocal detection channels that are coupled into the optical system using a dichroic beamsplitter. One channel detects the yellow-green emission from labeled fragments, and the other detects the red emission from labeled fragments. The DNA fragments are labeled with only two dyes which have been selected so that they have the same mobility shift during electrophoresis. In one example, the fluorescently labeled primers used in the production of the Sanger sequencing fragments were supplied by Applied Biosystems Inc. (Foster City, Calif.). The 5'-end of these primers are covalently attached to one of the two different fluorophores (FAM or JOE) which have similar absorption spectra and different emission spectra. The exact structure of these dyes is proprietary. However, the dyes fluorescein and NBD (Smith, et al., Nature, 321,674, 1986) have optical properties that are similar to those of FAM and JOE, respectively. Fragments labeled with JOE and FAM had substantially the same mobility shift in the capillary electrophoresis separation media.

The two-color capillary array electrophoresis scanner is shown in detail in FIG. 1. Light (488 nm; 6 mW) from an argon ion laser (Spectra-Physics 2020, Mountain View, Calif.), not shown, is reflected off a long-pass dichroic beamsplitter 11 (96% reflection for s-polarization at 488 nm, Omega Optical 480 DM, Brattleboro, Vt.) and directed through a 32×0.40 N.A. infinite conjugate objective 12 (Carl Zeiss LD Plan-Achromat 440850, Thornwood, N.Y.). The input beam diameter, 5 mm, is selected to give a 9 $\mu$m diameter spot in a given capillary. The micrometer adjustment 13 of the objective z-position is used to center the focused beam in the capillary. The fluorescence emission induced in the fluorophore by the laser beam is collected by the objective and passed back through the first beamsplitter (~92% transmission) to a second beamsplitter 14 (Omega Optical 565 DRLP) which separates the JOE and FAM emissions (fluorescence emission peaks at 557 nm and 530 nm, respectively). The two resulting beams are separately focused with 100 mm focal length achromat lens 17, 18 (Melles-Griot, Irvine, Calif.) through 400 $\mu$m diameter spatial filters 21, 22 (Melles-Griot) to effect confocal detection of the fluorescence emission. A bandpass discrimination filter with a transmission window of 525±5 nm (Omega Optical, 525ODF10) and 488 nm rejection band filter (Omega Optical, 488 RB) shown at 23, are placed in front of the photomultiplier 26 (RCA 31034A) dedicated to FAM detection while a bandpass discrimination filter, shown at 24, with a transmission window of 590±17 nm (Omega Optical, 590DF35) was placed in front of the photomultiplier 27 (RCA 31034A) dedicated to JOE detection. The outputs of the cooled phototubes 26, 27 are terminated (1 M$\Omega$), amplified and filtered (bandwidth ~DC to 300 Hz) with a low-pass filter-amplifier and digitized with a 12-bit ADC (Metra Byte DASH16-F, Taunton, Mass.) in an IBM PS2 computer. A computer-controlled dc servo motor-driven translation stage 31 (DCI4000, Franklin, Mass.) with a 6" travel and 2–5 $\mu$m resolution is used to translate the capillary array past the laser beam. Scanning of the capillary array is accomplished with periodic sweeps (1.4 s) of the array while sampling data at 1,500 samples per second per channel. With a line-scan rate of 2 cm/s, the physical dimension of the pixels acquired represent 13.3 $\mu$m. The computer is used to control the translation stage and to acquire and display images in a split screen format for the output of each detector. The fluorescence images are displayed in real time in pseudo-color and stored for processing.

Selected mole fractions of each of said sequencing fragment sets are synthesized using a primer labeled with a first fluorophore and different selected mole fractions of each of said fragment sets are synthesized using a primer labeled with a second fluorophore and the combined mole fractions are electrophoresed in a single capillary or lane and the fluorescence intensity is detected as a function of time as the DNA fragments move down the capillary.

One method for coding the sequencing fragments is binary coding. This is shown schematically in FIG. 2. The fragments terminating in A are synthesized using a 50/50 mixture of primers, half labeled with the red emitting (JOE) and half labeled with the green emitting (FAM) dye, and thus, carry the code (1,1). The G-fragments are synthesized using a primer that is just labeled with the red dye and carry the code (0,1), the T-fragments are synthesized with just the primer labeled with the green dye and carry the code (1,0) and the C-fragments are not labeled at all, carrying the code (0,0).

Binary coded DNA sequencing fragments were prepared through the following procedure: M13mp18 DNA sequencing fragments were produced using a Sequenase 2.0 kit (U.S. Biochemical Corp., Cleveland, Ohio). Commercially available FAM and JOE-tagged primers (400 nM, Applied Byosystems, Foster City, Calif.) were employed in the primer-template) annealing step. Three annealing solutions were prepared:

1. 4 $\mu$l of reaction buffer, 13 $\mu$l of M13mp18 single-stranded DNA, and 3 $\mu$l of FAM;
2. 6 $\mu$l of reaction buffer, 20 $\mu$l of M13mp18 DNA, 1.5 $\mu$l of FAM, and 3 $\mu$l of JOE;
3. 6 $\mu$l of reaction buffer, 20 $\mu$l of M13mp18 DNA, and 4.5 $\mu$l of JOE.

The tubes were heated to 65° C. for 3 minutes and then allowed to cool to room temperature for 30 minutes. When the temperature of the annealing reaction mixtures had dropped below 30° C., 2 $\mu$l of 0.1 M DTT solution, 4 $\mu$l of reaction buffer, and 10 $\mu$l of ddT termination mixture were added in tube 1; 3 $\mu$l of DTT solution, 6 $\mu$l of reaction buffer and 15 $\mu$l of ddA termination mixture were added in tube 2; and 3 $\mu$l of DTT, 6 $\mu$l of reaction buffer and 15 $\mu$l of ddG termination mixture were added in tube 3. Diluted Sequenase 2.0 (4 $\mu$l) was added in tube 1, and 6 $\mu$l of diluted Sequenase were added in tubes 2 and 3. The mixtures were incubated at 37° C. for 5 minutes. Ethanol precipitation was used to terminate the reaction and recover the DNA sequencing sample followed by resuspension and pooling in 6 $\mu$l of 80% (v/v) formamide. The sample was heated at 90° C. for 3 minutes and then placed on ice until sample injection.

Figure 3:
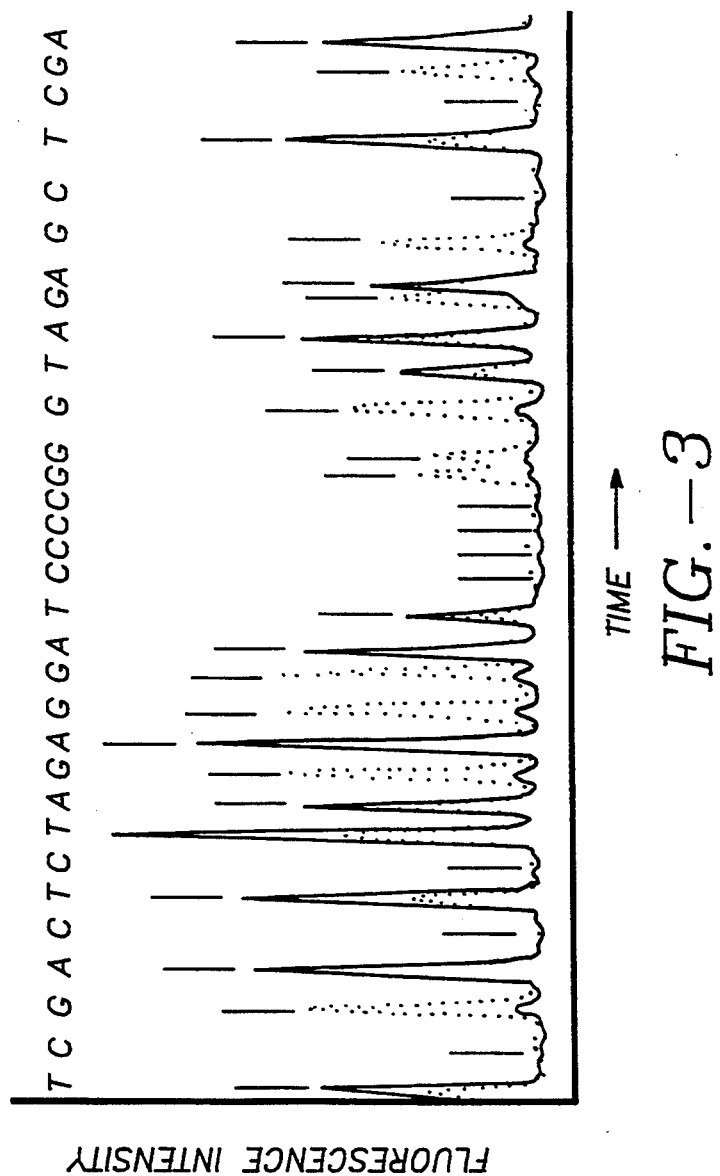
FIG. 3 is an example of the output using the labeled coding method of FIG. 2 in the apparatus of FIG. 1.

An example of the sequencing of DNA fragments employing this coding in the apparatus of FIG. 1 is shown in FIG. 3 where the outputs for the wavelengths in the above examples are overlapped. The sequence can be easily read off by examining the ratio of the green to the red signal intensity to determine the fragments G, A, T or C. When the red, represented by dotted curve, is largest, the fragment terminates in G;

when the green, represented by the solid curve, is much bigger than the red, it is a T; when the red and green are the same, it is an A; and when there is a gap, it is a C.

Figure 4:
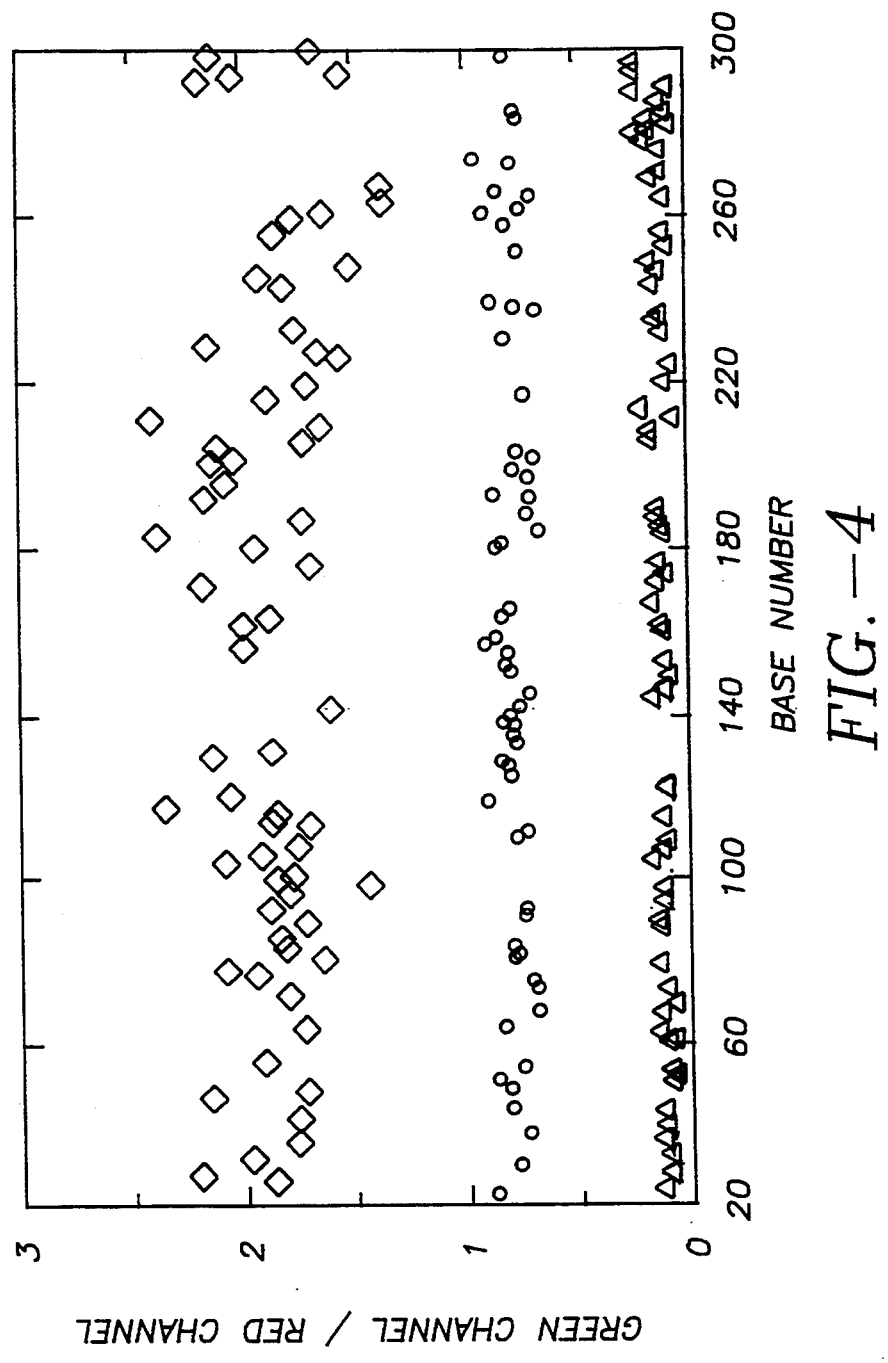
FIG. 4 is a plot of the ratio of fluorescence intensity using the labeled coding method of FIG. 2 and in the apparatus of FIG. 1.

The advantages of this labeling or coding method are: (1) The instrument design is simplified. Since there are only two optical detection channels, the optical efficiency is increased, giving a better signal-to-noise ratio. (2) With just two carefully selected dyes, there is no mobility shift of one set of base fragments relative to the other. This is clearly seen in FIG. 3, where the precise registration of the peaks in the red and green channels shows that the fragment migrations are essentially identical. (3) In the foregoing example, only two dye-labeled primers are needed. Thus, the number of labeled primers that must be synthesized is reduced. (4) Since the ratio of the signal in the green and red channels is used to identify the base, the base calling is not sensitive to changes in the optical alignment, laser intensity, or to the amount of the DNA fragments that migrate in a particular band. The latter point is very important since the termination reaction has different efficiency depending on where the termination occurs in the sequence. FIG. 4 is a plot of the fluorescence intensity in the green channel divided by that in the red channel for approximately 300 bases in an M13mp18 DNA sequencing run. The T fragments were labeled solely with FAM, the G fragments were labeled solely with JOE, and the A fragments were labeled with FAM and JOE. The ratio was calculated based on peak maxima. The diamonds represent labeled T fragments, the triangles represent labeled G fragments and the dots represent labeled A fragments. It is seen that the ratio provides an excellent determination of the identity of the fragments.

Of course it is to be realized that the labeling of the sets of DNA sequencing fragments can also be performed by labeling the dideoxy nucleotide terminator used in the sequencing reactions with a fluorescent label (Prober et al., Science 238, 336 (1987)) as opposed to labeling the primer. In this case, selected mole fractions of each of said sequencing fragment sets are synthesized using a terminator labeled with a first fluorophore and different selected mole fractions of each of said fragment sets are synthesized using a terminator labeled with a second fluorophore and the combined mole fractions are electrophoresed in a single lane or capillary, and the fluorescence intensity is detected at the characteristic emission wavelengths of the first and second fluorophores. The ratio of the intensities at the two wavelengths then determines the identity and sequence of the DNA. It is obvious that the different coding methods developed with labeled primers can also be implemented using dye-labeled terminators.

Of course, a variety of coding algorithms can be used along with this ratio detection. For example, some workers might object to the binary coding since the C-fragments are not explicitly detected. This can be resolved in several ways.

1. A second sequencing run can be done on the same DNA strand where the binary coding is simply permuted. Then A would be (0,0); G would be (0,1); T would be (1,0) and C would be (1,1). Since we can run a very large number of lanes on the capillaries, determining the sequence twice is not a problem.
2. One could sequence the complementary strand using the binary coding algorithm in FIG. 2. The presence of a C on the original strand would now be detected as a G on the complementary strand using the (0,1) coding.
3. Finally, one could use a modified labeling algorithm where all the fragments are labeled with a dye, but the relative amounts of the two dyes are adjusted to give four distinctive ratios for the green to the red channel. As depicted in FIG. 5, this coding would be specified by, for example, A (1,0); G (1,1); T (1,2); and C (0,1). In this case, the A fragments would only be labeled with the green dye; half of the G fragments would be labeled with the green and half with red; ⅓ of the T fragments would be labeled with the green dye and ⅔ with the red dye; finally, all the C fragments would be labeled with the red dye.

Since the ratio of the signals is used, three dyes that have the same mobility shift effect as one another can be used and various mixtures of three dyes can be used to label the primers to produce four sets of DNA sequencing fragments. The two-channel detection method with a ratio read out would still be used but by using three dyes in mixtures. The important point here is the concept of using ratio detection to code for all four base fragments on one capillary using only two detector channels.

Finally, it is clear that this method is not limited to fluorescence. For example, different ratios of two or more different isotopic labels could be employed. That is, the DNA sequencing fragments terminating in G, A, T and C can be coded by labeling the fragments with different ratios of isotopes. The labeled fragments could then be detected through measurements of radioactive emissions at two different energies, if the isotopes were radioactive, or by using mass spectrometer detection of ratios of stable isotopes.

What is claimed is:

1. A method of determining the sequence of DNA which comprises the steps of
    processing said DNA to form four sets of DNA sequencing fragments where one set contains fragments terminating in G, a second set contains fragments terminating in A, a third set contains fragments terminating in T, and a fourth set contains fragments terminating in C, such that selected mole fractions of each one of selected sets of sequencing fragments is tagged with a first fluorophore which fluoresces at a first wavelength and such that different selected mole fractions of each one of selected sets of sequencing fragments is tagged with a second fluorophore which fluoresces at a second wavelength and in which one of said sets of sequencing fragments is comprised of a mixture of selected mole fractions of fragments where one mole fraction is labeled with the first fluorophore and the other mole fraction is labeled with the second fluorophore,
    separating said sets of tagged DNA sequencing fragments in a single channel or lane, and
    determining the sequence of said sequencing fragments by detecting the ratio of fluorescence intensity at the first and second wavelengths as a function of time or position.

2. The method of claim 1 where the separation is performed electrophoretically in a capillary, gel-filled capillary or slab gel.

3. The method of claim 1 where the tagging of the sets of DNA sequencing fragments with the first and second fluorophores is performed by synthesizing a selected set of sequencing fragments by using selected mole fractions of two DNA primers, one of which is labeled with the first fluorophore and the other of which is labeled with the second fluorophore.

4. The method of claim 1 where the tagging of the sets of DNA sequencing fragments with the first and second fluorophores is performed by using selected mole fractions of two different fluorescently labeled terminators in the synthesis of the selected set of sequencing fragments, one of which is labeled with the first fluorophore and the other of which is labeled with the second fluorophore.

5. The method of claim 3 in which one of the sets of DNA sequencing fragments is synthesized with equal mole fraction ratios of primers labeled with the first and second fluorophores, a second one of the sets of DNA sequencing fragments is synthesized with a unity mole fraction of a primer labeled with the first fluorophore, a third one of the sets of DNA sequencing fragments is synthesized with a unity mole fraction of a primer labeled with the second fluorophore, and the fourth one of the sets of DNA sequencing fragments is unlabeled.

6. The method of claim 4 in which one of the sets of DNA sequencing fragments is synthesized with equal mole fractions of terminators labeled with the first and second fluorophores, a second of the sets of DNA sequencing fragments is synthesized with a unity mole fraction of a terminator labeled with the first fluorophore, a third of the sets of DNA sequencing fragments is synthesized with a unity mole fraction of a terminator labeled with a second fluorophore, and the fourth of the sets of DNA sequencing fragments is unlabeled.

7. The method of claims 5 or 6 in which the sequencing fragments terminating in G, A, T and C are identified by determining the ratio of intensity of the fluorescence at the first and second wavelength.

8. The method of claim 3 in which a first of said sets of DNA sequencing fragments is synthesized with unity mole fraction of primer labeled with a first fluorophore, a second of said sets of DNA sequencing fragments is synthesized with unity mole fraction of primer labeled with a second fluorophore, a third of said sets of DNA sequencing fragments is synthesized with equal mole fractions of primers labeled with said first and second fluorophores and the fourth set of DNA sequencing fragments is synthesized with unequal mole fractions of primers labeled with said first and second fluorophores.

9. The method of claim 4 in which a first of said sets of DNA sequencing fragments is synthesized with unity mole fraction of terminator labeled with a first fluorophore, a second of said sets of DNA sequencing fragments is synthesized with unity mole fraction of a terminator labeled with a second fluorophore, a third of said sets of DNA sequencing fragments synthesized with equal mole fractions of terminators labeled with said first and second fluorophores and the fourth set of DNA sequencing fragments is synthesized with unequal mole fractions of terminators labeled with said first and second fluorophores.

10. The method of claims 8 or 9 in which the sequencing fragments terminating in G, A, T and C are identified by determining the ratio of intensity of the fluorescence at the first and second wavelength.

11. The method as in claims 8 or 9 in which each of the sets of DNA fragments is coded with a different mole fraction ratio of the fluorophores that emit at first and second wavelengths.

12. A method of determining the sequence of DNA which comprises the steps of
processing sets of DNA sequencing fragments such that different selected mole fractions of each one of selected sets of sequencing fragments is tagged with fluorophores which emit fluorescence at different wavelengths with one of said sets of sequencing fragments is comprised of a mixture of selected mole fractions of fragments where one mole fraction is labeled with a fluorophore which fluoresces at a first wavelength and the other mole fraction is labeled with a fluorophore which fluoresces at a second wavelength,
separating said sets of tagged DNA sequencing fragments in a single channel or lane, and
determining the sequence of each of said sequencing fragments by detecting the ratio of fluorescence intensity at different wavelengths as a function of time or position.

13. The method of claim 12 where the separation is performed electrophoretically in a capillary, gel-filled capillary or slab gel.

14. The method of claim 12 in which the tagging is performed by synthesizing the DNA sequencing fragments using labeled DNA primers.

15. The method of claim 12 in which the tagging is performed by terminating the synthesis of the DNA sequencing fragments using dye-labeled terminators.

16. The method of claims 14 or 15 in which the fluorophores are selected to emit fluorescence at two wavelengths.

17. The method of claims 14 or 15 in which the fluorophores are selected to emit fluorescence at three wavelengths.

18. A method of determining the sequence of DNA which comprises the steps of
processing sets of DNA sequencing fragments terminating in G, A, T and C, where each one of said selected sets of sequencing fragments is labeled with a selected ratio of two or more radio-isotopes having the same mobility shift and one set of sequencing fragments is comprised of a mixture of selected mole fractions of fragments, one of which is labeled with one radio-isotope and the other of which is labeled with a second radio-isotope,
separating said sets of tagged DNA sequencing fragments in a single channel or lane, and
determining the sequence of said sequencing fragments by detecting the ratio of isotopes as a function of position or time.

19. The method of claim 18 where the separation is performed electrophoretically in a capillary, gel-filled capillary, or slab gel.

20. The method of claim 18 where the isotopes are radioactive and they are detected based on the different energy of their radioactive emission.

21. The method of claim 18 where the isotopes are stable and they are detected by using a mass spectrometer.

22. A method of determining the sequence of DNA which comprises the steps of
processing sets of DNA sequencing fragments where one set contains fragments terminating in G, a second set contains fragments terminating in A, a third set contains fragments terminating in T, and a fourth set contains fragments terminating in C, tagging selected mole fractions of each one of selected sets of sequencing fragments with a first tag which provides a first signal, tagging different selected mole fractions of each one of selected sets of sequencing fragments with a second tag which provides a second signal, tagging two different mole fractions of one set of sequencing fragment with two different tags which simultaneously provide first and second signals, separating said sets of tagged DNA sequencing fragments in a single channel or lane, and determining the sequence of said sequencing fragments by detecting the ratio of intensity of the first and second signals as a function of time or position.

* * * * *